US00RE45810E

(19) United States
(12) Reissued Patent
Yaginuma et al.

(10) Patent Number: US RE45,810 E
(45) Date of Reissued Patent: Nov. 24, 2015

(54) PROCESS FOR PRODUCING SPHERICAL BASE GRANULE COMPRISING EASILY WATER-SOLUBLE DRUG

(71) Applicant: ASAHI KASEI CHEMICALS CORPORATION, Tokyo (JP)

(72) Inventors: Yoshihito Yaginuma, Tokyo (JP); Rika Matsumoto, Tokyo (JP)

(73) Assignee: ASAHI KASEI CHEMICALS CORPORATION, Tokyo (JP)

(21) Appl. No.: 14/448,344

(22) Filed: Jul. 31, 2014

Related U.S. Patent Documents

Reissue of:
(64) Patent No.: 8,568,785
Issued: Oct. 29, 2013
Appl. No.: 12/309,351
PCT Filed: Jul. 18, 2007
PCT No.: PCT/JP2007/064200
§ 371 (c)(1),
(2) Date: Jan. 15, 2009
PCT Pub. No.: WO2008/010524
PCT Pub. Date: Jan. 24, 2008

(30) Foreign Application Priority Data

Jul. 19, 2006 (JP) ..... 2006-196947

(51) Int. Cl.
*A61K 9/16* (2006.01)
*A61K 9/36* (2006.01)
*A61K 31/192* (2006.01)
*A61K 31/4402* (2006.01)

(52) U.S. Cl.
CPC ..... *A61K 9/1676* (2013.01); *A61K 9/1623* (2013.01); *A61K 9/1652* (2013.01); *A61K 9/1694* (2013.01); *A61K 31/192* (2013.01); *A61K 31/4402* (2013.01)

(58) Field of Classification Search
None
See application file for complete search history.

(56) References Cited

U.S. PATENT DOCUMENTS

| | | | | |
|---|---|---|---|---|
| 5,026,560 | A | 6/1991 | Makino et al. | |
| 5,505,983 | A * | 4/1996 | Kamada | 427/2.21 |
| 5,766,623 | A * | 6/1998 | Ayres et al. | 424/441 |
| 6,015,789 | A | 1/2000 | Suzuki et al. | |
| 6,096,728 | A * | 8/2000 | Collins et al. | 514/62 |
| 6,149,943 | A * | 11/2000 | McTeigue et al. | 424/494 |
| 6,328,994 | B1 | 12/2001 | Shimizu et al. | |
| 2004/0043964 | A1 * | 3/2004 | Gomi et al. | 514/57 |

FOREIGN PATENT DOCUMENTS

| | | |
|---|---|---|
| CA | 2 591 761 | 7/2006 |
| JP | 63-301816 | 12/1988 |

(Continued)

OTHER PUBLICATIONS

Volland, Walt, "Solubility: How solubility is measured," Online Introductory Chemistry (http://www.800mainstreet.com/9/0009-004-solub.html), last revised Mar. 29, 2005.
International Search Report mailed on Sep. 18, 2007 for corresponding International Application No. PCT/JP2007/064200.
Solubility. Online Introductory Chemistry, 2005.*

(Continued)

*Primary Examiner* — Timothy Speer
(74) *Attorney, Agent, or Firm* — Staas & Halsey LLP

(57) ABSTRACT

Provided is a process for producing spherical base granules comprising a easily water-soluble drug and suited for film coating by spraying a layering liquid over pharmaceutically inert spherical core particles, thereby coating the particles with a layer comprising the easily water-soluble drug, wherein (1) the spherical core particles have a microcrystalline cellulose content of 30 mass % or greater and a water absorbing capacity of 0.5 $cm^3/g$ or greater; and (2) the layering liquid is an aqueous solution comprising at least the easily water-soluble drug and a low water-soluble saccharide.

6 Claims, 1 Drawing Sheet

(56) References Cited

FOREIGN PATENT DOCUMENTS

| | | |
|---|---|---|
| JP | 5-92918 | 4/1993 |
| JP | 7-53355 | 2/1995 |
| JP | 9-165329 | 6/1997 |
| JP | 10-45625 | 2/1998 |
| JP | 2000-281564 | 10/2000 |
| JP | 2003-24001 | 1/2003 |
| JP | 2003-509439 | 3/2003 |
| JP | 2006-16329 | 1/2006 |

OTHER PUBLICATIONS

International Search Report mailed on Sep. 18, 2007 in connection with International Application No. PCT/JP2007/064200.

English Translation of International Preliminary Report on Patentability issued on Feb. 19, 2009 in corresponding International Patent Application PCT/JP2007/064200.

European Search Report for corresponding European Patent Application No. 07790954.7, mailed on Jul. 5, 2013, 3 pages.

* cited by examiner

PROCESS FOR PRODUCING SPHERICAL BASE GRANULE COMPRISING EASILY WATER-SOLUBLE DRUG

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This [application] is *a reissue of U.S. application Ser. No. 12/309,351, issued as U.S. Pat. No. 8,568,785, which* claims the benefit under 35 U.S.C. Section 371 of International Application No. PCT/JP2007/064200, filed Jul. 18, 2007, which claimed priority to Japanese Application No. 2006-196947, filed Jul. 19, 2006 in the Japanese Patent Office, the disclosures of all of which are hereby incorporated by reference.

TECHNICAL FIELD

The present invention relates to a production process of spherical base granules comprising an easily water-soluble drug.

BACKGROUND ART

Pharmaceutical solid preparations are sometimes coated with sustained release coating, enteric coating or bitter-taste masking coating with a view to reducing side-effects of the drug comprising in them, reducing the administration frequency, improving the effect of the drug, suppressing bitter taste, stabilizing the drug, or the like. Granules having a high sphericity are one of the dosage forms suited for film coating thereon. Such granules are called spherical base granules.

As a production process of spherical base granules, a process of carrying out extrusion granulation using a drug and an excipient as raw materials and then spheronizing the resulting granules (extrusion/spheronization process), a process of coating the surface of spherical core particles with a drug (layering process) (refer to, for example, Patent Document 1 and Patent Document 2), and the like are known.

In the layering process, granules are produced by spraying a layering liquid to spherical core particles to coat the spherical core particles with a coating layer. Specific examples of it include a process (power coating process) of simultaneously supplying a drug in powder form and an aqueous solution of a binder; and a process (layering-liquid spraying process) of supplying a suspension of drug particles or an aqueous solution of the drug.

The layering process is suited as a process for producing spherical base granules, because spherical base granules having a high sphericity and a narrow particle size distribution can be obtained by using spherical core particles having a high sphericity and a narrow particle size distribution.

Among the layering processes, the powder coating process has low flexibility with respect to coating conditions and has relative difficulty in stable and high-yield production of spherical base granules. The layering-liquid spraying process is, on the other hand, a superior layering process because of easy condition setting and high productivity. In particular, when the layering-liquid spraying process is applied to the production of spherical base granules comprising a drug having a medium level of water solubility, spherical base granules excellent in various physical properties can be obtained in a high production yield by using a suspension of the drug as the layering liquid.

When the layering-liquid spraying process is applied to a production process of spherical base granules comprising a drug (easily water-soluble drug) having high water solubility, however, agglomeration of the spherical base granules is likely to occur. It is therefore necessary to reduce the concentration of the layering liquid or reduce the spray rate of the layering liquid.

The reduction in the concentration or spray rate of the layering liquid causes problems such as surface roughening due to a reduction in a filling density of a drug-comprising layer and a reduction in the mechanical strength of the spherical base granules. In addition, it leads to prolongation of a layering time and causes a further problem such as reduction in the production efficiency of the spherical base granules.

Under present circumstances, it is therefore very difficult to apply the layering process to the production of spherical base granules comprising an easily water-soluble drug.

It is known to add various additives to the layering liquid for the purpose of preventing agglomeration, preventing separation of layered drug controlling a dissolution rate of the drug, or stabilization (refer to, for example, Patent Document 3 or Patent Document 4). These prior arts are not developed for preventing agglomeration when an easily water-soluble drug is used and therefore do not have a sufficient effect for preventing agglomeration when a easily water-soluble drug is used. Moreover, when an inorganic substance is added, continuous stirring of the layering liquid is required in order to prevent precipitation.

Patent Document 1: Japanese Patent Laid-Open No. Sho 63-301816

Patent Document 2: Japanese Patent Laid-Open No. Hei 7-53355

Patent Document 3: Japanese Patent Laid-Open No. Hei 9-165329

Patent Document 4: Published Japanese Translations of PCT International Patent Publication No. 2003-509439.

DISCLOSURE OF THE INVENTION

Problems to be Solved by the Invention

An object of the present invention is to provide a production process of spherical base granules comprising a drug in accordance with a layering process, which production process can produce spherical base granules having a smooth surface and therefore suited for film coating without causing agglomeration of the spherical base granules even when the drug is easily water soluble.

Means for Solving the Problem

The present inventors have carried out an extensive investigation with a view toward overcoming the above-described problem. As a result, it has been found that agglomeration of particles can be suppressed greatly by using specific spherical core particles and adding a low water-soluble saccharide to a layering liquid comprising an easily water-soluble drug, leading to the completion of the present invention.

When a drug is easily water soluble, it is a common practice to overcome the problem of tackiness of the layering liquid by using a water insoluble additive. Unexpectedly, however, the tackiness of the layering liquid can be improved by the addition of a water soluble compound though its solubility is low.

In the present invention, there is thus provided a process for producing spherical base granules comprising a easily water-soluble drug by spraying a layering liquid over pharmaceutically inert spherical core particles, thereby coating them with a layer comprising the drug, wherein:

(1) the spherical core particles have a microcrystalline cellulose content of 30 mass % or greater and a water absorbing capacity of 0.5 $cm^3/g$ or greater; and (2) the layering liquid is an aqueous solution comprising at least the easily water-soluble drug and a low water-soluble saccharide.

Advantage of the Invention

The process according to the present invention enables efficient production of spherical base granules comprising an easily water-soluble drug with a smooth surface and high mechanical strength, because agglomeration of the spherical base granules can be prevented even without reducing the concentration or spray rate of the layering liquid.

BEST MODE FOR CARRYING OUT THE INVENTION

The present invention will hereinafter be described specifically.

First, the spherical core particles to be used in the invention are described.

The term "spherical" as used herein means particles having a sphericity (=short diameter/long diameter) of 0.7 or greater. Particles which are not spherical are not preferred because they deteriorate the uniformity of film coating. The spherical particles have preferably a sphericity of 0.9 or greater.

The spherical core particles have a microcrystalline cellulose content of 30 mass % or greater based on a total mass of the particles.

When the microcrystalline cellulose content is less than 30 mass %, it is difficult to obtain spherical core particles and at the same time, the particles have reduced strength. The microcrystalline cellulose content is preferably 70 mass % or greater, more preferably 100 mass %.

The term "microcrystalline cellulose" as used herein means microcrystalline cellulose which conforms to the standard of "microcrystalline cellulose" specified in the Japanese Pharmacopoeia Fourteenth Edition.

The spherical core particles are pharmaceutically inert, meaning that they do not comprise a drug.

It should be noted that the term "drug" as used herein means what is used for treatment, prevention, or diagnosis of human or animal diseases but what is not an instrument/machine.

The spherical core particles may comprise another pharmaceutical additive.

Examples of the another pharmaceutical additive include excipients such as lactose, sucrose, D-mannitol, corn starch, powdered cellulose, calcium hydrogen phosphate, and calcium carbonate; disintegrants such as low-substituted hydroxypropyl cellulose, carmellose calcium, pregelatinized starch, croscarmellose sodium, crospovidone, and carboxymethyl starch; binders such as hydroxypropyl cellulose, povidone (polyvinylpyrrolidone), and xanthan gum; coating agents such as hydroxypropylmethyl cellulose, methacrylic acid copolymer LD, and ethylcellulose aqueous dispersion; emulsifiers such as sucrose fatty acid ester, glycerin fatty acid ester, sodium lauryl sulfate, and polysorbate 60; and other additives such as talc, magnesium stearate, magnesium aluminometa silicate, titanium oxide, light silicic anhydride, microcrystalline cellulose and carboxymethylcellulose sodium.

The spherical core particles have a water absorbing capacity of 0.5 $cm_3/g$ or greater. The term "water absorbing capacity" as used herein means the volume of water which the spherical core particles can retain therein per unit mass and it is represented by the following equation:

$$\text{Water absorbing capacity } G\ [cm^3/g] = H/W$$

H: volume [$cm^3/g$] of water which spherical core particles can retain therein.

W: mass [g] of the spherical core particles.

Described specifically, it can be determined by adding 30 mL of purified water to 10 g of a sample (in terms of a dried sample), leaving the resulting mixture as is at room temperature for one hour, natural filtering out the solid through a filter paper, lightly wiping off water attached to the surface of the solid mass with another filter paper, measuring the mass of the solid, and dividing a difference calculated by subtracting 10 from the mass (water content) by 10.

When the water absorbing capacity is smaller than 0.5 $cm^3/g$, severe agglomeration of particles occurs during layering. The water absorbing capacity of 0.7 $cm^3/g$ or greater is preferred because it suppresses agglomeration effectively. The water absorbing capacity of 0.9 $cm^3/g$ or greater is more preferred.

No limitation is imposed on the water absorbing capacity from the viewpoint of agglomeration. However the particles which have swelled with water absorbed therein shrink during drying step after they are coated with a drug-containing layer, leading to deterioration in the strength of the resulting spherical base granules. The preferred maximum water absorbing capacity of particles, which do not swell even after water absorption, is about 1.8 $cm^3/g$.

The spherical core particles have an average particle size of preferably from about 50 to 1000 μm. The particle size distribution is preferably sharp. The spherical core particles have a (tapped) bulk density of preferably from about 0.5 to 2.0g/$cm^3$, though it depends on the balance of strength and water absorbing capacity. The spherical core particles composed only of microcrystalline cellulose have a bulk density of preferably from about 0.5 to 1.0 g/$cm^3$.

The mechanical strength of the spherical core particles is preferably higher.

The layering liquid to be used in the present invention will hereinafter be described.

The layering liquid comprises at least an easily water-soluble drug and a low water-soluble saccharide.

The term "easily water-soluble drug" as used herein means a drug having a solubility of 1 g or greater in 1 $cm^3$ of water at 20° C.

Conventionally, it was considerably difficult to adopt the layering process for producing spherical base granules with a high production yield when the easily water-soluble drug contained had a solubility of 1.5 g or greater. The present invention enables adoption of the layering process for the production of granules comprising such a easily water-soluble drug.

Examples of the easily water-soluble drug to be used in the present invention include chlorpheniramine d-maleate, ethyl L-cysteine hydrochloride, chloperastine hydrochloride, fasudil hydrochloride, procainamide hydrochloride, ceftizoxime sodium, tradipine, migrenin, and loxoprofen sodium.

The term "low water-soluble saccharide" as used herein means a saccharide having a solubility of 0.8 g or less in 1 $cm^3$ of water at 20° C. Examples of it include monosaccharides, disaccharides, oligosaccharides, and sugar alcohols. Preferred are D-mannitol, maltose, and lactose. They may be used either singly or in combination. Of these, D-mannitol is especially preferred.

The layering liquid has a content of the easily water-soluble drug of preferably from 5 to 30 mass % based on the total mass of the layering liquid. The layering liquid has a content of the low water-soluble saccharide of preferably from 1 to 30 mass %, more preferably from 3 to 20 mass %, still more preferably from 4 to 10 mass %. Since the solubility of D-mannitol in 1 $cm^3$ of water at 20° C. is 0.18 g, when it is used as the low water-soluble saccharide, its content is preferably from 1 to 15 mass %, more preferably from 3 to 12 mass %, especially preferably from 4 to 10 mass %.

If necessary, the layering liquid may comprise another pharmaceutical additive. Addition of a binder is especially preferred because it contributes to improvement in the strength of a layer comprising the easily water-soluble drug. Examples of such a binder include hydroxypropyl cellulose, povidone, and hydroxypropylmethyl cellulose.

The coating amount with the layer comprising the easily water-soluble drug can adequately be determined depending on the formulation design such as single dosage or size of the preparation. For example, the coating amount of the drug is generally from about 0.5 to 200 mass % based on the spherical core particles.

The production process of the spherical base granules according to the present invention will hereinafter be described.

A fluidized-bed coating apparatus can be used for coating the spherical core particles with the easily water-soluble drug containing layer. Examples of the fluidized bed coating apparatus include not only an ordinarily fluidized bed type but also, for example, a spouted bed type having, inside thereof, a guide tube (Wurster column) and a tumbling fluidized bed type equipped, on the bottom thereof, a rotation mechanism.

Specific examples of such apparatuses include "Flow Coater" and "Spiral Flow", products of Freund Corporation, "WST/WSG Series" and "GPCC Series", products of Glatt GmbH, "New Marumerizer", product of Fuji Paudal Co., Ltd., and "Multiplex", product of Powrex Corporation.

The layering liquid can be sprayed by a method suited for each of apparatuses such as top spray, bottom spray, side spray, and tangential spray. It may be sprayed to the spherical core particles continuously or intermittently.

After completion of spraying, the spherical base granules are dried. Drying of the spherical base granules may be performed as are or after controlling the air flow or temperature as needed while not taking out the granules from the apparatus.

The coating rate (spray rate of layering liquid) of the easily water-soluble drug layer is preferably 0.8 g/min or greater, in terms of an amount of a solid content of the layering liquid, per kg of the spherical core particles. Such a spray rate enables densification of the easily water-soluble drug containing layer and smoothing of the surface and as a result, spherical base granules suited for film coating can be obtained. In addition, such a spray rate enables a decrease in the layering time and improvement in the production efficiency.

The coating rate is more preferably 1.0 g/min or greater, more preferably 1.3 g/min or greater.

Next, one example of a production method of the spherical base granules will be described.

(a) Preparation of layering liquid: A layering liquid is prepared by adding a low water-soluble saccharide to water, thoroughly stirring the resulting mixture to dissolve the low water-soluble saccharide, adding an easily water-soluble drug and, if necessary, a pharmaceutical additive to the aqueous solution, and stir and dissolve (suspend) the resulting mixture sufficiently.

(b) Heating of spherical core particles and fluidized-bed coating apparatus: After spherical core particles are charged in a fluidized-bed coating apparatus, the core particles are caused to flow (when a fluidized-bed type coating apparatus with rotating equipment is employed, the rotating portion of it is turned simultaneously) by supplying hot air from the bottom portion of the apparatus until the outlet-air temperature reaches a predetermined temperature.

(c) Coating with drug containing layer: The layering liquid is sprayed at a predetermined spray rate continuously or intermittently or at a rate raised in a stepwise fashion. The supply of the layering liquid is terminated when the coating amount reaches a predetermined amount.

(d) Drying of spherical base granules: The spherical base granules are dried while adjusting the amount of hot air and temperature (rotation speed of the rotating portion when a tumbling fluidized bed type is employed) if necessary.

(e) Taking-out of spherical base granules: In the end, the resulting spherical base granules are taken out.

The spherical base granules obtained by the present invention can be used as granules, capsules, tablets or the like after subjected to particle size regulation and sustained release film coating, enteric film coating, or bitter-taste masking film coating if necessary.

Example 1

The present invention will next be described based on some examples. First, measuring methods of physical properties are described collectively.

<Sphericity [-] of Spherical Core Particles and Spherical Base Granules>

The shape of a sample is photographed using a digital microscope ("VH-7000", product of KEYENCE CORPORATION) (with a 50× or 100× lens) and a short diameter (D) and a long diameter (L) of 50 particles are measured using an image analyzer ("Image Hyper", product of Inter Quest). The terms "short diameter" and "long diameter" as used herein mean a short side and a long side of a minimum (in area) circumscribed rectangle of boundary pixels of a particle, respectively. The sphericity is an average of a short diameter/long diameter (D/L) ratio <Average Particle Size [μm] of Spherical Core Particles>

The average particle size is defined as a value at 50% in the cumulative distribution of the small diameter (D) determined in the same manner as the measuring method of a sphericity.

<Water Absorbing Capacity [$cm^3$/G] of Spherical Core Particles>

It can be determined in the following manner 30 mL of purified water is added to 10 g (in terms of a dried sample) of a sample. After the resulting mixture is left as is at room temperature for one hour, the resulting mixture is naturally filtered through a filter paper to separate a solid and water attached to the surface of the solid mass is wiped off lightly with another filter paper. Then, the sample is weighed and the amount of contained water is divided by 10. The above-described operation is repeated five times and an average is adopted as the water absorbing capacity.

<Tapped Bulk Density [g/$Cm^3$] of Spherical Core Particles>

A 100 $cm^3$ graduated cylinder is filled with 30 g of a sample and a tapped volume [$cm^3$] after tapping about 30 times is measured. The tapped bulk density is calculated in accordance with the following equation. This operation is repeated three times and an average is adopted as a tapped bulk density.

Apparent tapped bulk density [g/cm$^3$]=30 [g]/tapped volume [cm$^3$].

<Recovery Ratio [Mass %] of Spherical Base Granules>

The recovery ratio is determined in accordance with the following equation based on the recovery amount [g] of spherical base granules after layering and total amount [g] of raw materials employed.

Recovery ratio [mass %]=(recovery amount [g]/total amount [g] of raw materials)×100

<Agglomeration Ratio [%] of Spherical Base Granules>

After dispersion of spherical base granules on paper, the number [a] of particles constituting agglomerated granules and the number [b] of single isolated particles are counted visually. The agglomeration ratio is calculated in accordance with the following equation. The number of particles observed is 1000 (=a+b).

Agglomeration ratio [%]={a/(a+b)}×100

<Tackiness [-]>

A layering liquid (3 g) is poured in a polypropylene Petri dish having a diameter of 8 cm and dried at 40° C. in an air-circulation-free dryer ("FC610", product of Advantec Co., Ltd.). Within three seconds after taking out the dried product from the dryer, tackiness of the dried film when an index finger is pressed against the film for two seconds and then released therefrom is evaluated by a panel of three experts. The tackiness is rated as "1" when no tackiness is observed, "2" when a little tackiness is observed, "3" when tackiness is observed, "4" when strong tackiness is observed, and "5" when very strong tackiness is observed. The tackiness of the dried film is evaluated by the average of them.

It is known empirically that agglomeration occurs during layering when the tackiness is "3" or higher so that the layering rate must be set low to prevent it. Layering cannot be performed in practice when the tackiness is "5".

Example 1

(Preparation of Layering Liquid)

6.0 g of D-mannitol (product of Towa Kasei Kogyo Co., Ltd.) of a low water-soluble saccharide was added to 99.6 g of water while stirring with propeller. The resulting mixture was stirred until completely dissolved. Then, 2.4 g of povidone ("K-30", product of ISP Tec. Inc.) and 12.0 g of chlorpheniramine d-maleate (product of Kongo Chemical Co., Ltd.) were added as a binder and an easily water-soluble drug, respectively, then the resulting mixture was stirred until completely dissolved to yield a layering liquid.

(Production of Spherical Base Granules)

Spherical base granules having a sphericity of 0.94 were obtained by charging 0.6 kg of spherical core particles consisting of 100% microcrystalline cellulose ("CELPHERE" CP-203, product of Asahi Kasei Chemicals Corporation, water absorbing capacity: 1.0 cm$^3$/g, average particle size: 237 μm, sphericity: 0.90, tapped bulk density: 0.96 g/cm$^3$) in a tumbling fluidized-bed coating apparatus ("Multiplex" MP-01, product of Powrex Corporation) and layering the spherical core particles with the layering liquid by using a tangential bottom spray until the coating amount reached 3.4 mass % (2.0 mass % in terms of the drug) under the conditions of a spray air pressure of 0.16 MPa, a spray air flow rate of 40 L/min, a inlet-air temperature of 80° C., an outlet-air temperature of from 45 to 46° C., an air flow of from 37 to 50 m$^3$/h, and a spray rate of layering liquid of 5.0 g/min (corresponding to the coating rate of 1.4 g/min in terms of a solid content per kg of spherical core particles). During production, the rotation speed of the rotor was adjusted to 400 rpm until the layering amount reached 1.7 mass % and then adjusted 450 rpm until the layering amount reached 3.4 mass %. After that, the rotation speed of the rotor was reduced to 200 rpm and drying was performed until the outlet-air temperature increased to 48° C. A heater for charge air was then turned off and cooling was performed until the outlet-air temperature decreased to 40° C.

The spherical base granules thus obtained scarcely attached to the inside wall of the coating apparatus and a substantially whole amount of them was collected.

Example 2

(Preparation of Layering Liquid)

The same layering liquid used in Example 1 was used.

(Production of Spherical Base Granules)

Spherical base granules having a sphericity of 0.94 were obtained by charging a Wurster coating apparatus ("Multiplex" MP-01 using a Wurster column, product of Powrex Corporation) with 0.3 kg of the same spherical core particles as employed in Example 1 and layering the spherical core particles with the layering liquid until the layering amount reached 3.4 mass % (2.0 mass % in terms of the drug) under the conditions of spray air pressure of 0.16 MPa, spray air flow rate of 40 L/min, inlet-air temperature of 75° C., outlet-air temperature of from 42 to 49° C., air flow of from 31 to 43 m$^3$/h, and spray rate of layering liquid of 2.5 g/min (corresponding to the coating rate of 1.4 g/min in terms of a solid content per kg of spherical core particles).

Example 3

(Preparation of Layering Liquid)

1.5 g of D-mannitol was added to 51.3 g of water while stirring with propeller. The resulting mixture was stirred until completely dissolved. Then 1.2 g of povidone and 6.0 g of chlorpheniramine d-maleate were added therein, and the resulting mixture was stirred until completely dissolved to obtain a layering liquid.

(Production of Spherical Base Granules)

In the same manner as Example 2 except that layering of the spherical core particles was performed at a spray rate of the layering liquid of 2.5 g/min (corresponding to a coating rate of 1.2 g/min in terms of a solid content per kg of spherical core particles) until the coating amount reached 2.9 mass % (2.0 mass % in terms of the drug), spherical base granules having a sphericity of 0.93 were obtained.

Example 4

(Preparation of layering liquid)

0.3 g of D-mannitol was added to 52.5 g of water while stirring with propeller, and stirring was continued until completely dissolved. Then 1.2 g of povidone and 6.0 g of chlorpheniramine d-maleate were added therein, and the resulting mixture was stirred until completely dissolved to obtain a layering liquid.

(Production of Spherical Base Granules)

In the same manner as Example 2 except that layering of the spherical core particles was performed at a spray rate of the layering liquid of 2.5 g/min (corresponding to a coating speed of 1.0 g/min per kg of spherical core particles) until the layering amount reached 2.5 mass % (2.0 mass % in terms of the drug), spherical base granules having a sphericity of 0.92 were obtained.

Example 5

(Preparation of Layering Liquid)

13.0 g of D-mannitol was added to 81.0 g of water while stirring with propeller, and stirring was continued until completely dissolved. Then 1.0 g of povidone and 5.0 g of chlorpheniramine d-maleate therein were added, and the resulting mixture was stirred until completely dissolved to obtain a layering liquid.

(Production of Spherical Base Granules)

In the same manner as Example 2 except that layering of the spherical core particles was performed at a spray rate of the layering liquid of 2.0 g/min (corresponding to a coating rate of 1.3 g/min in terms of a solid content per kg of spherical core particles) until the layering amount reached 7.6 mass % (2.0 mass % in terms of the drug), spherical base granules having a sphericity of 0.96 were obtained.

Example 6

(Preparation of Layering Liquid)

1.5 g of lactose ("Pharmatose 200M", product of DMV) was added to 51.3 g of water while stirring with propeller, and stirring was continued until completely dissolved. Then, 1.2 g of povidone and 6.0 g of phenylchloramine d-maleate were added therein, and the resulting mixture was stirred until completely dissolved to obtain a layering liquid.

(Production of Spherical Base Granules)

In the same manner as Example 2 except that layering of the spherical core particles was performed at a spray rate of the layering liquid of 2.5 g/min (corresponding to a coating rate of 1.2 g/min in terms of a solid content per kg of spherical core particles) until the layering amount reached 2.9 mass % (2.0 mass % in terms of the drug), spherical base granules having a sphericity of 0.91 were obtained.

Comparative Example 1

(Preparation of Layering Liquid)

In the same manner as Example 1 except that D-mannitol was not added, a layering liquid was prepared. Described specifically, 2.4 g of povidone as a binder and 12.0 g of chlorpheniramine d-maleate were added to 105.6 g of water while stirring with propeller and the resulting mixture was stirred until completely dissolved to obtain a layering liquid.

(Production of Spherical Base Granules)

In the same manner as Example 1 except that layering of the spherical core particles was performed until the layering amount reached 2.4 mass % (2.0 mass % in terms of the drug) under the conditions of an outlet-air temperature of from 42 to 46° C., an air flow of from 40 to 55 $m^3$/h, and a spray rate of the layering liquid of 5.0 g/min (corresponding to a coating rate of 1.0 g/min in terms of a solid content per kg of spherical core particles), spherical base granules having a sphericity of 0.92 were obtained. The rotation speed of a rotor was adjusted to 400 rpm until the layering amount reached 1.2 mass % and then adjusted to 450 rpm until the layering amount reached 2.4 mass %.

Since the spherical base granules had high tackiness and attached to the inside of the coating apparatus, their recovery ratio was low.

Comparative Example 2

In the same manner as Comparative Example 1 except that the spray rate of the layering liquid was adjusted to 2.5 g/min (corresponding to a coating rate of 0.5 g/min in terms of a solid content per kg of spherical core particles), spherical base granules having a sphericity of 0.92 were obtained.

Comparative Example 3

(Preparation of Layering Liquid)

The same layering liquid as employed in Comparative Example 1 was used.

(Production of Spherical Base Granules)

It was tried to carry out layering of spherical core particles until the layering amount reached 2.4 mass % (2.0 mass % in terms of the drug) in the same manner to Example 4, but operation was terminated because the spherical base formed a mass on the bottom of the column when the layering amount reached 0.84 mass %, thus stopped flowing.

Comparative Example 4

(Preparation of Layering Liquid)

A layering liquid was prepared in the same manner as Example 1.

(Production of Spherical Base Granules)

It was tried to carry out layering of spherical core particles until the layering amount reached 3.4 mass % (2.0 mass % in terms of the drug) in the same manner to Example 2 except that spherical granules ("Nonpareil" NP-101, grain size: 32-42 type, product of Freund Corporation, average particle size: 423 μm, sphericity: 0.91) composed of purified sucrose and corn starch was used as the spherical core particles. The spherical base granules formed a mass on the bottom of the column when the layering amount reached 1.7 mass %, thus stopped flowing so that operation was terminated.

The results of Examples 1 to 6, and Comparative Examples 1 to 4 are shown in Table 1.

The layering liquids obtained in Examples 1 to 6 according to the present invention each showed low tackiness, and the recovery ratio was high and low agglomeration of the spherical base granules was observed.

In contrast, the layering liquids obtained in Comparative Examples 1 to 3 which comprised no low water-soluble saccharide showed high tackiness. As a result, the spherical base granules thus obtained had high tackiness and attached to the inside wall of the apparatus, leading to a low recovery ratio. Moreover, the agglomeration ratio was high, thus the spherical base granules were not suited for film coating.

In Comparative Example 3 in which a Wurster column (guide tube) was used, the spherical base granules formed a mass on the bottom of the column, which prevented completion of layering.

In Comparative Example 4 in which the spherical core particles comprising no microcrystalline cellulose were used, the spherical base granules obtained had high tackiness in spite of low tackiness of the layering liquid so that layering was not completed.

TABLE 1

| | Composition of spherical core particles Microcrystalline cellulose [mass %] | Composition of layering liquid: Easily water-soluble drug [mass %] | Composition of layering liquid: Low water-soluble saccharide [mass %] | Coating rate** [g/min] | Tackiness* of layering liquid | Agglomeration of base granule [%] | Recovery ratio of base granule [%] |
|---|---|---|---|---|---|---|---|
| Example 1 | 100 | 10 | 5 | 1.4 | 1(1, 1, 1) | 9.8 | 97.6 |
| Example 2 | 100 | 10 | 5 | 1.4 | 1(1, 1, 1) | 6.1 | 95.5 |
| Example 3 | 100 | 10 | 2.5 | 1.2 | 1(1, 1, 1) | 8.9 | 93.7 |
| Example 4 | 100 | 10 | 0.5 | 1.0 | 2(2, 1, 2) | 9.9 | 90.4 |
| Example 5 | 100 | 5 | 13 | 1.3 | 1(1, 1, 1) | 9.2 | 90.2 |
| Example 6 | 100 | 10 | 2.5 | 1.2 | 1(1, 1, 1) | 11.3 | 89.6 |
| Comp. Ex. 1 | 100 | 10 | 0 | 1.0 | 4(4, 4, 4) | 34.4 | 73.7 |
| Comp. Ex. 2 | 100 | 10 | 0 | 0.5 | 4(4, 4, 4) | 25.2 | 95.5 |
| Comp. Ex. 3 | 100 | 10 | 0 | 1.0 | 4(4, 4, 4) | Interruption of layering | |
| Comp. Ex. 4 | 0 | 10 | 5 | 1.4 | 1(1, 1, 1) | Interruption of layering | |

*Numerals in the parenthesis under tackiness are evaluation by a panel of experts.
**Solid content per kg of spherical core particles.

SEM photographs of the spherical base granules obtained in Example 1 and an example of unagglomerated spherical base granules obtained in Comparative Examples 1 and 2 are shown in FIGS. 1 to 3.

The spherical base granules obtained in Example 1 and Comparative Example 1, both of which had a high spray rate of the layering liquid, had a smooth surface, while the spherical base granules obtained in Comparative Example 2, which had a low spray rate, had a surface inferior in smoothness.

Referential Example 1

5.0 g of lactose ("Pharmatose" 200M, product of DMV) as a low water-soluble saccharide was added to 83.0 g of water while stirring with propeller, and the resulting mixture was stirred until completely dissolved. Then, 2.0 g of polyvinylpyrrolidone and 10.0 g of chlorpheniramine d-maleate as an easily water-soluble drug were added, and the resulting mixture was stirred until completely dissolved. The tackiness of the layering liquid was measured.

Referential Example 2

In the same manner as Referential Example 1 except that maltose (product of Wako Pure Chemical Industries) was used as the low water-soluble saccharide instead of lactose, a layering liquid was prepared and tackiness thereof was measured.

Referential Example 1

5.0 g of lactose ("Pharmatose" 200M, product of DMV) as a low water-soluble saccharide was added to 83.0 g of water while stirring with propeller, and the resulting mixture was stirred until completely dissolved. Then, 2.0 g of polyvinylpyrrolidone and 10.0 g of chlorpheniramine d-maleate as an easily water-soluble drug were added, and the resulting mixture was stirred until completely dissolved. The tackiness of the layering liquid was measured.

Referential Comparative Example 2

In the same manner as Referential Example 1 except that fructose (product of Wako Pure Chemical Industries) (solubility in 1 $cm^3$ of water: 0.6 g) which was not a low water-soluble saccharide was used instead of lactose, a layering liquid was prepared and tackiness thereof was measured.

Referential Example 3

5.0 g of lactose was added to 88.0 g of water while stirring with propeller and the resulting mixture was stirred until completely dissolved. Then, 2.0 g of polyvinylpyrrolidone and 10.0 g of loxoprofen sodium (product of OHARA Pharmaceutical Co., Ltd.) which was an easily water-soluble drug were added and the resulting mixture was stirred until completely dissolved. The tackiness of the resulting solution was measured.

Referential Comparative Example 3

2.0 g of polyvinylpyrrolidone and 10.0 g of loxoprofen sodium were added to 88.0 g of water while stirring with propeller. The resulting mixture was stirred until completely dissolved and the tackiness of the solution was measured.

Referential Comparative Example 4

In the same manner as Referential Example 3 except that sorbitol was used instead of lactose, a layering liquid was prepared and tackiness thereof was measured.

Referential Comparative Example 5

In the same manner as Referential Example 3 except that fructose was used instead of lactose, a layering liquid was prepared and tackiness was measured.

The composition and tackiness of each of the layering liquids obtained in Referential Examples 1 to 3 and Referential Comparative Examples 1 to 5 are shown in Table 2.

The layering liquids of Referential Examples 1 to 3 comprising a low water-soluble saccharide had low tackiness irrespective of the kind of the easily water-soluble drug employed.

In contrast, the layering liquids of Referential Comparative Examples comprising no low water-soluble saccharide each had high tackiness. In particular, results of Referential Comparative Examples 1, 2, 4, and 5 have revealed that sorbitol and fructose which are high water-soluble do not show a tackiness reducing effect although they are saccharides.

TABLE 2

| | Composition of layering liquid | | | | | | |
|---|---|---|---|---|---|---|---|
| | | | Saccharide [mass %] | | | | |
| | Easily water-soluble drug [mass %] | | Low water solubility | | High water solubility | | |
| | Chlorpheniramine maleate | Loxoprofen sodium | Lactose (solubility** 0.19 g) | Maltose (solubility** 0.78 g) | Sorbitol (solubility** 0.9 g) | Fructose (solubility** 6 g) | Tackiness* of layering liquid |
| Ref. Ex. 1 | 10 | | 5 | | | | 1(1, 1, 1) |
| Ref. Ex. 2 | 10 | | | 5 | | | 1(1, 2, 1) |
| Ref. Comp. Ex. 1 | 10 | | | | 5 | | 5(5, 4, 5) |
| Ref. Comp. Ex. 2 | 10 | | | | | 5 | 5(4, 5, 5) |
| Ref. Ex. 3 | | 10 | 5 | | | | 1(2, 1, 1) |
| Ref. Comp. Ex. 3 | | 10 | | | | | 4(4, 4, 4) |
| Ref. Comp. Ex. 4 | | 10 | | | 5 | | 4(4, 4, 4) |
| Ref. Comp. Ex. 5 | | 10 | | | | 5 | 4(5, 4, 4) |

*Numerals in the parenthesis under tackiness are evaluation by a panel of experts

**Solubility in 1 $cm^3$ of water of 20° C.

INDUSTRIAL APPLICABILITY

The production process of the present invention is preferably employed in the field of production of pharmaceutical granules subjected to film coating.

LEGEND

None

Figure 1:
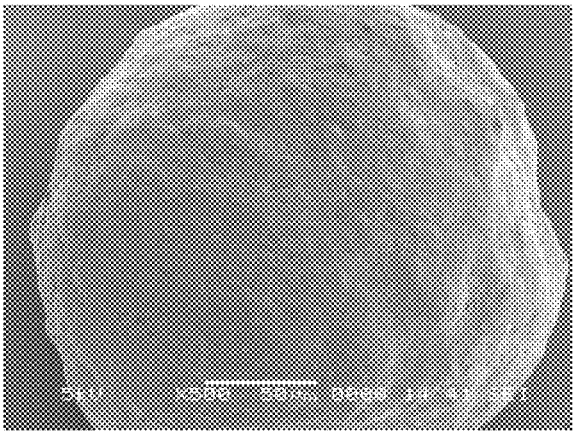
FIG. 1 Surface condition of spherical base granules obtained in Example 1.
Figure 2:
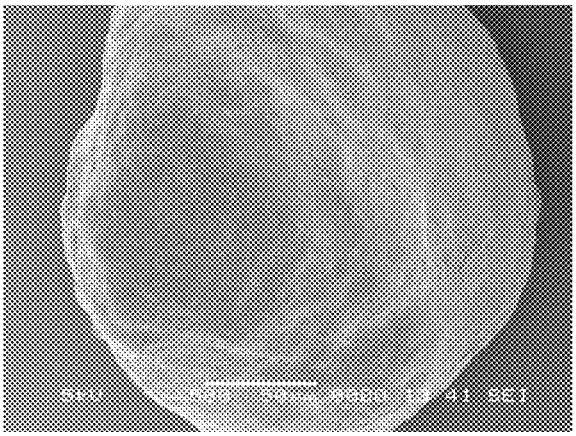
FIG. 2 Surface condition of spherical base granules obtained in Comparative Example 1.
Figure 3:
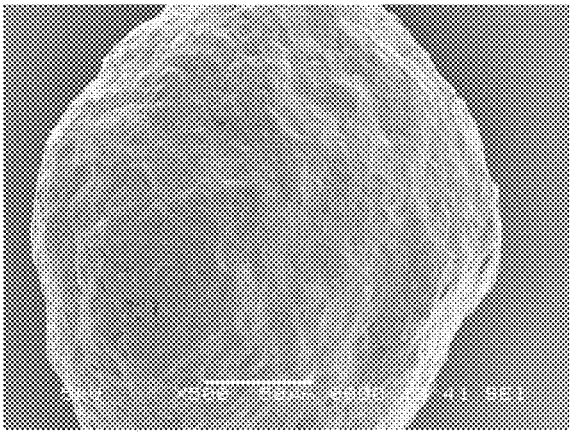
FIG. 3 Surface condition of spherical base granules obtained in Comparative Example 2.

The invention claimed is:

1. A process for producing spherical base granules comprising an easily water-soluble drug, which comprises spraying a layering liquid over pharmaceutically inert spherical core particles to thereby coat the particles with a drug-containing layer, wherein:

(1) the spherical core particles have a microcrystalline cellulose content of 30 mass % or greater, a water absorbing capacity of 0.5 $cm^3/g$ or greater and a bulk density of about 0.5 to about 2.0 $g/cm^3$;

(2) the layering liquid is an aqueous solution comprising at least from 5 to 30 mass % of the easily water-soluble drug and from 1 to 30 mass % of D-mannitol[;

(3) the easily water-soluble drug has a solubility of 1.5 g or greater in 1 $cm^3$ of water at 20° C.]; and

[(4)] (*3*) the easily water-soluble drug is at least one selected from the group consisting of ethyl L-cysteine hydrochloride, cloperastine hydrochloride, procainamide hydrochloride, ceftizoxime sodium, migrenin, and loxoprofen sodium.

2. The process for producing spherical base granules comprising an easily water-soluble drug according to claim 1, wherein the coating rate of the drug-containing layer is 0.8 g/min or greater per kg of the spherical core particles.

3. The process for producing spherical base granules comprising an easily water-soluble drug according to any one of claims 1 or 2, wherein the spherical core particles comprise microcrystalline cellulose in an amount of 70 mass % or greater.

4. The process for producing spherical base granules comprising an easily water-soluble drug according to claim 1 or 2, wherein the water absorbing capacity of the spherical core particles is 0.7 $cm^3/g$ or greater.

5. The process for producing spherical base granules comprising an easily water-soluble drug according to claim 1 or 2, wherein the layering liquid comprises from 5 to 20 mass % of the easily water-soluble drug and from 3 to 20 mass % of D-mannitol.

6. The process for producing spherical base granules comprising an easily water-soluble drug according to claim 1 or 2, wherein the layering liquid comprises from 1 to 15 mass % of D-mannitol.

* * * * *